Figure 1:
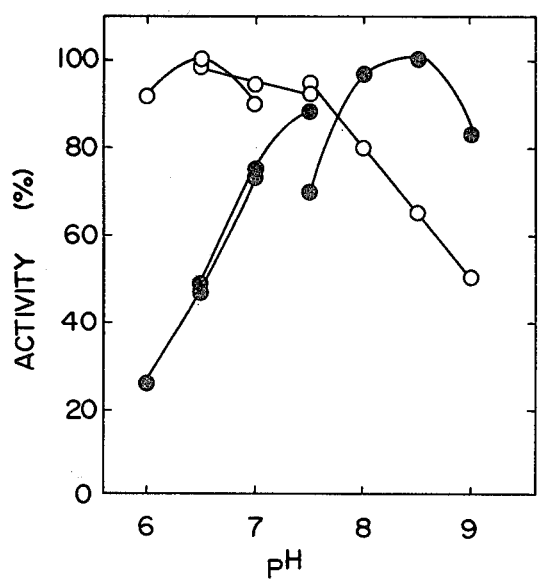

United States Patent [19]

Ikuta et al.

[11] 4,346,173
[45] Aug. 24, 1982

[54] PROCESS FOR THE PRODUCTION OF ACYL-COENZYME A OXIDASE

[75] Inventors: Shigeru Ikuta; Shigeyuki Imamura; Hidehiko Ishikawa; Kazuo Matsuura; Masaki Takada; Hideo Misaki, all of Shizuoka, Japan

[73] Assignee: Toyo Jozo Kabushiki Kaisha, Shizuoka, Japan

[21] Appl. No.: 201,123

[22] Filed: Oct. 27, 1980

[30] Foreign Application Priority Data

Oct. 26, 1979 [JP] Japan ................................ 54-139166

[51] Int. Cl.$^3$ .............................................. C12N 9/02
[52] U.S. Cl. .................................... 435/189; 435/830; 435/913; 435/942; 435/911
[58] Field of Search ........................ 435/183, 189, 192

[56] References Cited

FOREIGN PATENT DOCUMENTS 3007399 9/1980 Fed. Rep. of Germany ...... 435/189

OTHER PUBLICATIONS

Stokes et al., A Soluble acyl–Coenzyme A Oxidase from the Yeast *Candida utilis*, Archives of Biochemistry and Biophysics, vol. 176, pp. 591-603 (1976).

*Primary Examiner*—Raymond N. Jones
*Assistant Examiner*—John E. Tarcza
*Attorney, Agent, or Firm*—Young & Thompson

[57] ABSTRACT

A process for the production of acyl-Coenzyme A oxidase, comprises culturing an acyl-Coenzyme A-oxidase-producing microorganism belonging to genus Macrophomina, genus Cladosporium, genus Aspergillus, genus Monascus, genus Saccharomyces or genus Arthrobacter in a nutrient medium, and isolating the thus-formed acyl-CoA oxidase therefrom. The preferred species of microorganism are *Macrophomina phaseoli* ATCC 14383, *Cladosporium resinae* IFO 6367, *Aspergillus candidus* M-4815 FERM-P No. 5226, *Monascus* sp. M-4800 FERM-P No. 5225, *Saccharomyces cerevisiae* Y 0036 FERM-P No. 5174, and *Arthrobacter* sp. B-720 FERM-P No. 5224, respectively.

7 Claims, 3 Drawing Figures

PROCESS FOR THE PRODUCTION OF ACYL-COENZYME A OXIDASE

This invention relates to a process for the production of acyl-Coenzyme A oxidase (hereinafter acyl-CoA oxidase).

Acyl-CoA oxidase is an enzyme which catalyzes a reaction in which one mole of acyl-CoA consumes one mole of oxygen to generate one mole of 2,3-dehydroacyl-CoA and one mole of hydrogen peroxide.

A known microorganism which produces acyl-CoA oxidase is *Candida utilis.* [Arch. Biochem. Biophys., 176, 591-603 (1976)].

We have found that mold belonging to genus Macrophomina, strain *Macrophomina phaseoli* ATCC 14383 [The American Type Culture Collection Catalogue of Strains I (1978)]; genus Cladosporium, strain *Cladosporium resinae* IFO 6367 [Institute for Fermentation OSAKA List of Cultures (1978)]; genus Aspergillus, strain *Aspergillus candidus* M-4815; and genus Monascus, strain Monascus sp. M-4800; yeast belonging to genus Saccharomyces, strain *Saccharomlyces cerevisiae* Y 0036; and bacteria belonging to genus Arthrobacter, strain Arthrobacter sp. B-0720, produce acyl-CoA oxidase; and we have isolated the said enzyme.

The taxonomical properties of the above microorganisms are as follows:

1. *Aspergillus candidus* M-4815:
   A. Growth conditions on various media:
      (1) Czapeck agar:
         Growth at 26° C.: slow, 15-18 mm in diameter after 10 days culture.
         Colonies: thin and flat. Color of colony: white at early stage, cream (hue 1½ Ca) to pale yellow (hue 1 Ca) at mature stage with many conidia. No formation of sclerotia. Reverse of colony: colorless. No production of diffusible pigment or exudate.
      (2) Malt extract agar:
         Growth at 26° C.: moderate, 42-45 mm in diameter after 10 days culture.
         Colonies: thin and flat. Color of colony: white at early stage, cream (hue 1½ Ca) at mature stage with many conidia. Reverse of colony: colorless. No production of diffusible pigment or exudate.
   B. Microscopic observation:
      Conidial head: white to cream, comparatively large, 500-800μ in diameter, globose at early stage forming several radials at mature stage. Conidiophore: 500-1000μ in length, 8-15μ in width, smooth walled. Vesicle: globose to subglobose, 20-40μ in diameter. Sterigma: two layers. Primary sterigma: 5.0-12.0×3.0-4.0μ, secondary sterigma: 5.0-7.0×2.5-3.0μ. Conidia: globose, 2.5-3.5μ, smooth walled.
   C. Physiological properties:
      Growth pH: 3-11
      Growth temperature: 15°-37° C.

Referring to the above taxonomical properties, the strain M 4815, having vesicles on the top of the conidia, many sterigma on the vesicles and a single-cell conidia chain on the top of vesicles, is confirmed to belong to the genus Aspergillus. This strain, having large conidial heads and abundant white to creamy conidia, is referred to as *Aspergillus candidus* [K. B. Raper and D. I. Fennell, *The Genus Aspergillus,* 686 pp. (1965), J. A. von Arx, *The Genera of Fungi Sporulating In Pure Culture,* 315 pp. (1974)] and is designated as *Aspergillus candidus* M-4815. This strain has been deposited in the Institute for Industrial Microbial Technology and Science, M.I.T.I., Japan (hereinafter designated as the Fermentation Institute) as permanent culture collection FERM-P No. 5226.

2. Monascus sp. M-4800:
   A. Growth conditions on various media:
      (1) Malt extract agar:
         Growth at 26° C.: rapid, 60-65 mm in diameter after 10 days culture.
         Colonies: thin and flat. Flocculent white aerial hyphae grown at early stage of culture, the flocculent disappearing depending on culture progress. Color: coral (hue 7 lc). Reverse of colony: brick red (hue 6 ng).
      (2) Potato glucose agar:
         Growth at 26° C.: rapid, 60-63 mm in diameter after 10 days culture.
         Colony: thin and flat, center slightly elevated. Flocculent white aerial hyphae grown at early stage of culture, the flocculent disappearing depending on culture progress. Color: colonial rose (hue 7 ic). Reverse of colony: brick red (hue 6 ng).
   B. Microscopic observation:
      Ascocarp: globose, 20-45μ in diameter, formed on the top of stem of 40-60×3-5μ. Ascospore: elliptical, 4.5-5.5×4-4.5μ, colorless, smooth walled.
      Conidia: Meristem-anthrospore type, formed chainwise on the top of conidia, obpyriform, colorless, 7-10μ in diameter.
   In the vegetative hyphae, reddish brown pigment is formed.
   C. Physiological properties:
      (1) Optimum growth conditions:
         Optimum growth pH; 4-9.
         Optimum growth temperature: 22°-30° C.
      (2) Growth conditions:
      Growth pH: 3-11.
      Growth temperature: 15°-35° C.

As hereinabove explained, the strain M-4800, forming globose ascocarp on the top of stem and the asci disappearing at an early stage, is identified as belonging to genus Monascus [*The Genera of Fungi Sporulating in Pure Culture,* 315 pp, (1974)] and is referred to as Monascus sp. M-4800. This strain has been deposited in the Fermentation Institute as permanent culture collection FERM-P No. 5225.

3. *Saccharomyces cerevisiae* Y 0036:
   A. Growth conditions on various media:
      (1) MY liquid medium:
         Good growth at 26° C. on the bottom of medium. No formation of pellicle. Slightly turbid on growth. No coloring of medium.
      (2) MY agar medium:
         Good growth at 26° C. Periphery of giant colonoy is entirely or partially undulate. Surface: several radial wrinkles. Dull luster. Butyrous in character. Cream color.
      (3) Slide culture on potato agar medium:
         Vegetable cells: 3.0-8.0×2.5-7.0μ. Asphericle, ovoid or elliptical. Growth by polypolar budding. No formation of hyphae or pseudophyphae.
   B. Formation of ascospore:

Good formation of ascospores on Gorodkwa medium. Globose or ovoid. Smooth surface. 2.5–3.0μ in diameter. 1–4 spores in one ascus.
C. Formation of radial spore: none.
D. Physiological properties:
  (1) Optimum growth conditions:
    Optimum growth pH: 3–7.
    Optimum growth temperature: 20°–30° C.
  (2) Growth range:
    Growth pH: 2–9.
    Growth temperature: 10°–40° C.
  (3) Nitrate assimilation: —
  (4) Decomposition of lipid: —
  (5) Decomposition of urea: —
  (6) Gelatin liquefaction: —
  (7) Antiosmotic pressure: growth limit in NaCl concentration 12–14%.
  (8) Formation of calotinoid: —
  (9) Typical organic acid formation: —
  (10) Formation of starch-like substance: —
  (11) Vitamin requirement: —
  (12) Fermentation and assimilation of sugar:

|  | Fermentative | Assimilable |
|---|---|---|
| D-arabinose |  | — |
| L-arabinose |  | — |
| D-ribose |  | — |
| D-xylose |  | — |
| D-glucose | + | + |
| D-mammose |  | + |
| D-galactose | + | + |
| D-rhamnose |  | — |
| D-fructose |  | + |
| L(-)-sorbose |  | — |
| maltose | + | + |
| sucrose | + | + |
| lactose | — | — |
| melibiose |  | — |
| cellobiose |  | — |
| trehalose |  | — |
| raffinose | ½+ | + |
| melezitose |  | + |
| arbutin |  | — |
| soluble starch |  | — |
| inulin |  | — |
| DL-lactate |  | + |
| succinate |  | + |
| citrate |  | + |

Referring to the above taxonomic properties, the strain Y 0036, having characteristics of yeast, globose or ovoid in shape, formation of smooth ascospore, growth of vegetative hyphae by polypolar budding, no formation of radial spore, no assimilation of nitrate and good fermentation of glucose, belongs to genus Saccharomyces. Further details on the morphology of the strain, growth, sugar fermentation and assimilation and other properties suggest the description as *Saccharomyces cerevisiae* [J. Lodder, *The Yeasts, a taxonomic study*, 1385 pp. (1950)]. This strain is accordingly referred to as *Saccharomyces cerevisiae* Y 0036 and has been deposited in the Fermentation Institute as permanent culture collection FERM-P No. 5174.

4. Arthrobacter sp. B-0720:
A. Growth on various media:
  (1) Nutrient agar plate:
    Colony: Circular, smooth periphery, convex, grayish white to pale yellow after 2–3 days culture.
  (2) Nutrient agar slant:
    Good growth, filiform growth. Diffusible pigment production after 2–3 days culture.
  (3) Bouillon broth:
    Weak growth, turbid, no pellicle formation.
  (4) BCP milk:
    Weakly alkaline after 5–7 days.
B. Microscopic observation:
  (1) Shape and size of cells:
    Young cells (six hours cultivation): straight or slightly curved rod or stick. A few branched cells. Old cells (20 hours cultivation): short rod or globose (polymorphism).
  Size:
    0.5–0.8 × 1.5–3.0μ (young cells)
    0.5–0.8 × 0.5–1.4μ (old cells)
  No formation of spore.
  (2) Motility: subpolar flagella or polar flagella.
C. Physiological properties:
  (1) Growth temperature:
    No growth at 10° C. Weak growth at 42° C. Good growth at 25°–35° C.
  (2) Growth pH: No growth at pH 6.0. Growth at pH 6.5–9.0.
  (3) Stain: Gram's strain: + Acid-fast stain: —
  (4) Cellulose decomposition: —
  (5) Gelatin decomposition: +
  (6) Casein decomposition: +
  (7) Esculin decomposition: +P2 (8) Starch hydrolysis: +
  (9) Catalase formation: +
  (10) Oxidase formation: +
  (11) Urease formation: —
  (12) Indole formation: —
  (13) H₂S formation: —
  (14) Acetoin formation: —
  (15) Nitrate reduction: +
  (16) Citrate utilization: +
  (17) Ammonium utilization: +
  (18) Nitrate utilization: +
  (19) O-F test*: O (oxidative)
  (20) Acid formation from sugar*:
    Acid formation (no gas formation): L(+)-arabinose, cellobiose, D-galactose, D-glucose, glycerol, lactose, D-mannose, starch, sucrose.
    No acid formation: adonitol, dulcitol, mesoerythritol, fucose, inositole, inulin, maltose, manntiol, melezitose, melibiose, raffinose, L(+)-rhamnose, salicin, L(—)-sorbose, sorbitol, trehalose.
*[J. Gen. Microbiol., 30, 400–420 (1963)].

As a result, the taxonomical properties of the strain B-0720 were identical with those of genus Arthrobacter [*Bergey's Manual of Determinative Bacteriology*, 8th Ed. (1974), Can. J. Microbiol., 20, 1411–1414 (1974)] as to positive Gram's strain, non acid-fast, polymorphism of aerobic bacteria and no cellulose decomposition. Therefore, the strain B-0720 is referred to as Arthrobacter sp. B-0720 and has been deposited in the Fermentation Institute as permanent culture collection FERM-P No. 5224.

The present invention provides a process for the production of acyl-CoA oxidase, which comprises culturing acyl-CoA-oxidase-producing microorganisms belonging to genus Macrophomina, genus Cladosporium, genus Aspergillus, genus Monascus, genus Saccharomyces or genus Arthrobacter in a nutrient medium, and isolating the produced enzyme.

The strain which can be used in the present invention is, for example, *Macrophomina phaseoli* ATCC 14383, *Cladosporium resinae* IFO 6367, *Aspergillus candidus* M-4815, Monascus sp. M-4800, *Saccharomyces cerevisiae* Y 0036 or Arthrobacter sp. B-0720. The invention is not limited to these strains, however, as other acyl-CoA-producing strains belonging to the above geni and natural or artificial mutants thereof can be used in the present invention.

In an embodiment of the present invention, one of the above acyl-CoA-oxidase-producing microorganisms is cultured in a conventional medium for enzyme production. The cultivation of the microorganisms can be carried out by liquid or solid culture. Submerged aeration culture is preferable for industrial production.

A conventional culture medium for microorganisms can preferably be used. As for the carbon sources, assimilable carbon sources such as glucose, galactose, molasses, starch hydrolysate, or a higher fatty acid such as oleic acid, palmitic acid, atearic acid, palmitoleic acid or myristoleic acid can be used. Assimilable nitrogen sources such as peptone, soybean powder, casein hydrolysate, corn steep liquor, meat extracts, yeast extract, nitrate or ammonium salt can be used. Various salts such as sodium chloride, potassium chloride, potassium phosphate or magnesium sulfate are optionally used. The addition of higher fatty acids such as oleic acid for carbon sources to the medium stimulates the production of acyl-CoA oxidase. The amount of addition is preferably 0.5–1% by weight of the medium.

The culturing temperature can be selected within the ranges for the growth of microorganisms and the production of enzymes, and is preferably 25°–30° C. for mold and 28°–33° C. for yeast or bacteria. The culturing time can be selected depending on conditions and is usually 40–100 hours for mold, 50–80 hours for yeast and 15–40 hours for bacteria. Culturing should naturally be terminated when the acyl-CoA oxidase production is substantially complete. Acyl-CoA oxidase is an endo-enzyme which exists in the cells of microorganisms.

Examples of the extraction of acyl-CoA oxidase from the cultured mass are as follows:

The cultured mass is filtered and the wet cells are suspended in a phosphate buffer or tris-HCl buffer, and disrupted by treatment with lysozyme, sonication or a French press. The thus-obtained crude acyl-CoA oxidase is purified by conventional isolation and purification methods for proteins and enzymes. For example, fractional precipitation with acetone, ethanol or isopropanol and salting out with ammonium sulfate are preferably used. Further purification can be achieved by, for example, electrophoresis or chromatography in which crude acyl-CoA oxidase is dissolved in phosphate buffer or tris-HCl buffer and chromatographed using ion exchangers such as diethylamino ethyl-cellulose (DEAE-cellulose) or -dextran gel, or gel filtration agents such as dextran gel or polyacrylamide gel. Purified acyl-CoA oxidase can be stored as a lyophilized powder.

Figure 2:
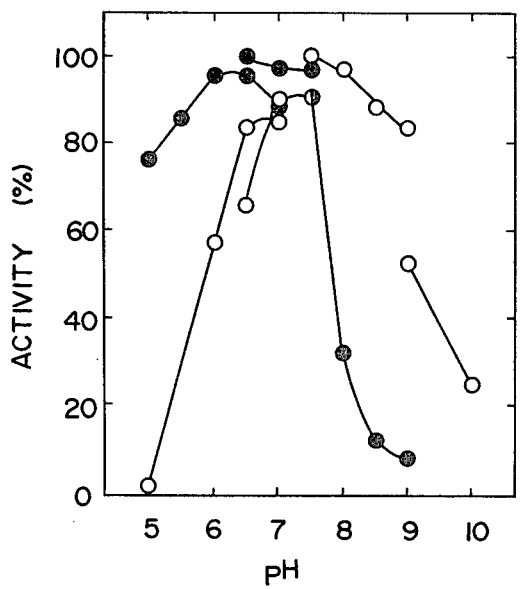
Figure 3:
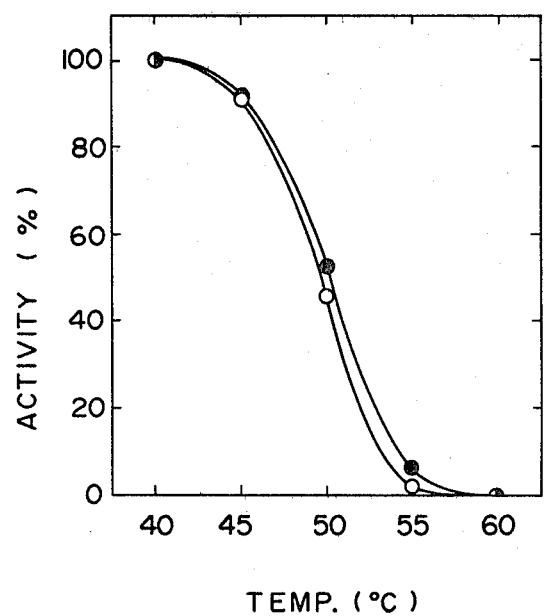

The accompanying drawings show three of the physicochemical properties of acyl-CoA produced by the present invention in which:

FIG. 1 is a graph of activity versus optimum pH;
FIG. 2 is a graph of activity versus pH stability; and
FIG. 3 is a graph of heat stability.

Acyl-CoA oxidase produced by the present invention is assayed by the following method and has the following physicochemical properties:

(1) Assay method:

Enzyme solution (10 μl) is added to a reaction mixture (0.5 ml) consisting of 0.2 M phosphate buffer (pH 7.0) or 0.2 M tris-HCl buffer (pH 8.0) (0.1 ml), 5 mM 4-aminoantipyrine (0.05 ml), 3 mM diethyl m-toludine (0.05 ml), peroxidase (0.5 mg/ml, 0.05 ml), 25 mM palmitoyl-CoA (0.02 ml) and distilled water (0.23 ml) and the mixture is incubated at 37° C. for 10 minutes. 4 M urea (0.5 ml) is added to stop the reaction, and 1% by weight of Triton X-100 (2 ml) is added thereto and the generated hydrogen peroxide is measured at 545 nm by colorimetry.

A unit (1 unit, 1 U) of enzyme activity is defined as the activity of enzyme which generates $1\mu$ mole of hydrogen peroxide per minute.

(2) Enzyme action:

Oxidation of one mole of acyl-CoA consumes one mole of oxygen and liberates one mole of 2,3-dehydroacyl-CoA and one mole of hydrogen peroxide.

(3) Optimum pH:

Optimum pH is determined by assaying enzyme activity in dimethylglutaryl buffer (pH 6.0–7.0), phosphate buffer (pH 6.5–7.5) and tris-HCl buffer (pH 7.5–9.0). Optimum pH of the enzyme is shown in the table that follows in the present text. The data from which these optimum values were derived are plotted on FIG. 1, in which:

⌐: Arthrobacter sp. B-0720
○: *Macrophomina phaseoli* ATCC 14383.

(4) pH stability:

Enzyme solution is added to buffers of various pH, incubated at 37° C. for 60 minutes, and the remaining activity is assayed. Phosphate buffer for pH 6.5–7.5, tris-HCl buffer for pH 7.5–9.0 and glycine buffer for pH 9.0–10.0 are used. The pH stability of acyl-CoA oxidase is shown in the table and the associated data plotted on FIG. 2, in which:

⌐: Arthrobacter sp. B-0720
○: *Macrophomina phaseoli* ATCC 14383.

(5) Heat stability:

Enzyme is heated at 40° C., 45° C., 50° C., 55° C. and 60° C. for 10 minutes, and the remaining enzyme activity is assayed. Results are shown in the table and the associated data plotted on FIG. 3, in which:

⌐: Arthrobacter sp. B-0720
○: *Macrophomina phaseoli* ATCC 14383.

(6) Km value: Shown in the table.
(7) Isoelectric point: Shown in the table.

As hereinabove explained, acyl-CoA oxidase of the present invention catalyzes the oxidation of long-chain acyl-CoA such as palmitoyl-CoA by consuming one mole of oxygen and generating 2,3-dehydroacyl-CoA and hydrogen peroxide.

The enzyme of the present invention can be used for analysis of fatty acid, CoA and triglyceride in acyl-CoA-forming systems, for example an acyl-CoA-forming system in a reaction mixture consisting of fatty acid, CoA and fatty-acid-activating enzyme and the fatty-acid-forming system consisting of triglyceride and lipase or lipoprotein lipase. The enzyme can also be used for assay of activity of fatty acid-activating-enzymes, lipase or lipoprotein lipase.

The following examples illustrate the present invention.

| Acyl—CoA producing microorganism | optimum pH | pH-stability | heat stability | Km | isoelectric point |
|---|---|---|---|---|---|
| Arthrobacter sp. B-0720 | 8.0–8.5 | 6.0–7.5 | <45° C. | 0.13 mM | 4.70 |
| Macrophomina phaseoli ATCC 14383 | 6.5–7.5 | 6.5–8.5 | <40° C. | 0.087 mM | 5.19 |
| Cladosporium resinae IFO 6367 | 6.5–7.5 | 6.5–8.0 | <40° C. | 0.12 mM | |
| Aspergillus candidus M-4815 | 6.5–7.5 | 6.5–8.5 | <40° C. | 0.11 mM | |
| Monascus sp. M-4800 | 6.5–8.0 | 6.5–8.0 | <40° C. | 0.15 mM | |
| Saccharomyces cerevisiae | around 8.0 | 6.0–10.0 | <45° C. | 0.50 mM | |

EXAMPLE 1

An aqueous medium (10 ml) comprising oleic acid 1% by weight, yeast extract 0.25% by weight, peptone 1% by weight, KCl 0.2% by weight, $K_2HPO_4$ 0.1% by weight, $MgSO_4.7H_2O$ 0.05% by weight and anti-foam agent (Disfoam BC-51Y) 0.2% by weight in a test tube was sterilized. Arthrobacter sp. B-0720 was inoculated therein and the mixture was shake cultured at 30° C. overnight. This seed culture was transferred to the same sterilized medium (5 lit.) in an 8-liter jet fermenter and cultured at 30° C. for 20 hours, at 600 r.p.m., with aeration of 5 l/min.

Bacterial cells centrifugally collected were suspended in a solution (1 lit.) consisting of 10 mM phosphate buffer (pH 7.0), 2 mM EDTA and lysozyme (0.5 mg/ml) and the suspension was stirred at 37° C. for 60 minutes. Deoxyribonuclease (5 mg) was added, and the mixture was further stirred for 10 minutes. To the supernatant obtained centrifugally at 10000 r.p.m. for 20 minutes was added acetone (200 ml) and the mixture was centrifuged. Acetone (1.8 lit.) was added to the superntant; then the precipitate, which was collected centrifugally, was dissolved in 10 mM phosphate buffer (200 ml, pH 7.0). Insoluble substance was removed by centrifugation and the supernatant was fractionated by adding saturated ammonium sulfate solution to 30–75% saturation. The precipitate was dissolved in 10 mM phosphate buffer (40 ml, pH 7.0) and desalted through a column of acrylamide gel (tradename; Biogel P-2, product of Biorad Co.) The desalted solution was introduced into a calcium phosphate gel column to adsorb the enzyme after washing out the non-adsorbed fraction, acyl-CoA oxidase was eluted by graduated 0.05—0.05 M phosphate buffers (pH 7.0). The active fraction (around 0.45 M) was collected and dialyzed and concentrated by ultrafiltration (tradename: Diaflow membrane PM-10, product of Amicon Co.), then lyophilized to obtain a powder of acyl-CoA oxidase. (Specific activity: 5.5 U/mg, Total activity: 850 U, yield: 8.5%).

EXAMPLE 2

An aqueous medium (10 ml) comprising oleic acid 1% by weight, yeast extract 0.25% by weight, defatted soybean powder (tradename: Protoflower) 1% by weight, KCl 0.2% by weight, $K_2HPO_4$ 0.1% by weight, $CaCO_3$ 0.5% by weight and anti-foam agent Disfoam BC-51Y 0.2% by weight in a test tube was sterilized. Macrophomina phaseoli ATCC 14383 was inoculated therein and the mixture was shake cultured at 26° C. for 4 days. The seed culture was transferred to the same medium (5 lit.) in an 8-liter jar fermenter and cultured at 26° C. for 45 hours, at 700 r.p.m., with aeration of 5 lit/min.

Fungal cells were obtained by filtration and were suspended in 10 mM phosphate buffer (pH 7.0, 1.5 lit.) The suspension was homogenized for 15 minutes. The supernatant obtained by centrifugation was concentrated in vacuo up to 1/10 volume to separate insolubles. Saturated ammonium sulfate solution was added to the supernatant to fractionate the same, to 30–80% saturation. The precipitate was dissolved in 10 mM phosphate buffer (pH 7.0, 75 ml), and further fractionated in 30–80% ammonium sulfate saturation. The thus-obtained precipitate was dissolved in phosphate buffer (pH 7.0, 40 ml) and insoluble materials were removed by centrifugation. The solution was charged on a column of Sephacryl S-300 (trade name: Pharmacia Fine Chem. Co.) and eluted to obtain the active fractions. The active fraction was concentrated with an ultra filtration membrane (Diaflow membrane XM-50, Amicon Co.) and lyophilized to obtain a powder of acyl-CoA oxidase (specific activity: 1.2 U/mg, total activity: 110 U, yield: 11.0%).

EXAMPLES 3–5

In Example 2, Macrophomina phaseoli ATCC 14383 was replaced by Aspergillus candidus M-4815, Cladosporium resinae IFO 6367 Monascus sp. M-4800, respectively, and these strains were respectively inoculated in the same medium (100 ml) as Example 2 in 500 ml Erlenmeyer flasks, and the mixture was shake cultured at 26° C. for 4 days. The filtered mycelia were suspended in 10 mM phosphate buffer (pH 7.0, 1/5 volume of suspension) and sonicated for 10 minutes. Acyl-CoA oxidase activities of the supernatent solutions obtained by centrifugation were assayed as follows:

| Microorganisms: | Enzyme activity (U/ml) |
|---|---|
| Aspergillus candidus M-4815 | 0.047 |
| Cladosporium resinae IFO 6367 | 0.035 |
| Monascus sp. M-4800 | 0.065 |

These were purified by the same procedure as in Example 1.

EXAMPLE 6

The strain Saccharomyces cerevisiae Y 0036 was inoculated in an aqueous medium (pH 4.2, 100 ml) comprising oleic acid 1% by weight, yeast extract 0.25% by weight, peptone 0.5% by weight, KCl 0.2% by weight, $KH_2PO_4$ 0.1% by weight and $MgSO_4.7H_2O$ 0.05% by weight in a 500 ml Erlenmeyer flask, and the mixture was shake cultured at 30° C. for 3 days. Yeast cells, which were collected by centrifugation, were suspended in 10 mM phosphate buffer (pH 7.0, 1/5 volume of the suspension) and sonicated for 10 minutes. Acyl-CoA oxidase activity in the supernatent solution obtained by centrifugation was 0.75 U/ml. Purification procedures were the same as in Example 1.

What is claimed is:

1. A process for the production of acyl-Coenzyme A oxidase, which comprises culturing an acyl-Coenzyme A-oxidase-producing microorganism belonging to genus Macrophomina, genus Cladosporium, genus Aspergillus, genus Monascus, genus Saccharomyces or genus Arthrobacter in a nutrient medium, and isolating the thus-formed acyl-CoA oxidase therefrom.

2. A process as claimed in claim 1, wherein the microorganism is *Macrophomina phaseoli* ATCC 14383.

3. A process as claimed in claim 1, wherein the microorganism is *Cladosporium resinae* IFO 6367.

4. A process as claimed in claim 1, wherein the microorganism is *Aspergillus candidus* M-4815 FERM-P No. 5226.

5. A process as claimed in claim 1, wherein the microorganism is Monascus sp. M-4800 FERM-P No. 5225.

6. A process as claimed in claim 1, wherein the microorganism is *Saccharomyces cerevisiae* Y 0036 FERM-P No. 5174.

7. A process as claimed in claim 1, wherein the microorganism is Arthrobacter sp. B-0720 FERM-P No. 5224.

* * * * *